United States Patent [19]

Connor et al.

[11] 4,018,781
[45] Apr. 19, 1977

[54] 2-ARYL SUBSTITUTED ISOXAZOLO(2,3-ALPHA)PYRIDINYL HALIDES

[75] Inventors: David T. Connor, Parsippany; Patricia A. Young, Madison; Maximilian von Strandtmann, Rockaway Township, all of N.J.

[73] Assignee: Warner-Lambert Company, Morris Plains, N.J.

[22] Filed: May 27, 1976

[21] Appl. No.: 690,478

Related U.S. Application Data

[62] Division of Ser. No. 611,281, Sept. 8, 1975, Pat. No. 3,983,237.

[52] U.S. Cl. .................. 260/297 B; 424/263; 260/295 F; 260/296 R
[51] Int. Cl.[2] .......................... C07D 498/00
[58] Field of Search .................. 260/297 B

[56] References Cited

UNITED STATES PATENTS 3,983,237  9/1976  Connor et al. .............. 424/263

OTHER PUBLICATIONS

Boekelheide et al., J. Org. Chem. vol. 26, pp. 3802 to 3805 (1961).
Adams et al., J. Am. Chem. Soc. vol. 79, pp. 2236 to 2239 (1957).
Boekelheide et al., J. Am. Chem. Soc. vol. 80, pp. 2217 to 2220 (1958).
Osborne et al., J. Heterocyclic Chemistry, vol. 1, pp. 138 to 140 (1964).

*Primary Examiner*—John D. Randolph
*Attorney, Agent, or Firm*—Albert H. Graddis; Frank S. Chow; Anne M. Kelly

[57] ABSTRACT

2-Aryl substituted isoxazolo[2,3-a]pyridinyl halides having the formula I:

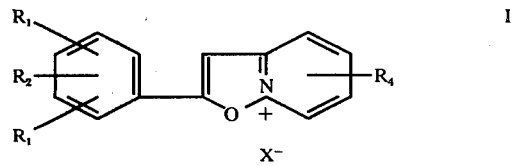

wherein $R_1$, $R_2$ and $R_3$ are each hydrogen, halogen, hydroxy, lower alkyl, lower alkoxy or lower alkanoyl; $R_4$ is hydrogen or lower alkyl; X is a bromide, chloride or iodide salt; the pharmaceutically acceptable, acid addition salts thereof; and processes for the preparation thereof, are described. The compounds of the invention are useful as anti-inflammatory agents and for the treatment of hyperacidity.

3 Claims, No Drawings

2-ARYL SUBSTITUTED ISOXAZOLO(2,3-ALPHA)PYRIDINYL HALIDES

This is a division of application Ser. No. 611,281 filed Sept. 8, 1975, now U.S. Pat No. 3,983,237 granted Sept. 28, 1976.

DESCRIPTION OF THE PRIOR ART

Osborne et al., in J. Heterocyclic Chem., 1: 138–140 (1964), describe the preparation of 1-phenyl-2-(2-pyridinyl)ethanone N-oxide by the acylation of 2-picoline N-oxide, using sodium amide in liquid ammonia as the condensing agent. No pharmacological activity is reported for this or related compounds described by Osborne et al.

DESCRIPTION OF THE PARTICULAR EMBODIMENTS

This invention relates to 2-aryl substituted isoxazolo[2,3-a]pyridinyl halides having the formula I:

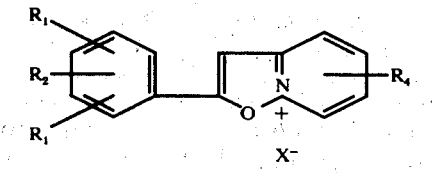

wherein $R_1$, $R_2$ and $R_3$ are each hydrogen, halogen, hydroxy, lower alkyl, lower alkoxy or lower alkanoyl; $R_4$ is hydrogen or lower alkyl; X is a bromide, chloride or iodide salt; and pharmaceutically acceptable acid addition salts thereof. Compounds of the formula I above, wherein $R_1$ is hydrogen, halogen, hydroxy, methyl, methoxy or acetoxy; $R_2$ is hydrogen, hydroxy, methyl, methoxy or acetoxy; $R_3$ is hydrogen or hydroxy; $R_4$ is hydrogen or methyl; and X is the bromide salt, as well as their pharmaceutically acceptable, acid addition salts, are particularly preferred.

The compounds of the formula II:

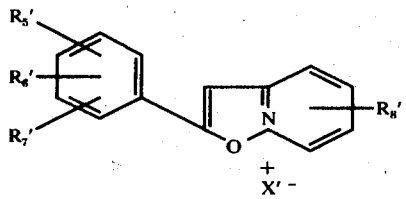

wherein $R_5'$, $R_6'$ and $R_7'$ are each hydrogen, halogen, hydroxy, lower alkyl or lower alkoxy; $R_8'$ is hydrogen or lower alkyl; and X' is a bromide, chloride or iodide salt, are prepared by treating a compound of the formula III:

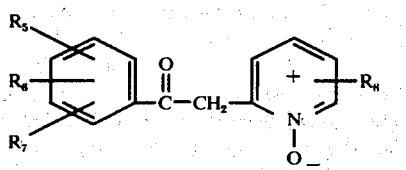

wherein $R_5$, $R_6$ and $R_7$ are each hydrogen, halogen, hydroxy, lower alkyl or lower alkoxy and $R_8$ is hydrogen or lower alkyl, with a hydrohalide acid and a lower alkanoic acid to effect ring closure. In the course of this reaction, one or more lower alkoxy substituents on compound III is converted into a hydroxy substituent on final compound II unless certain other protective substituents are present in specific positions. Thus, it appears that a protective effect is exerted by a halogen group, positioned para to the lower alkoxy group on the phenyl ring of compound III. Additionally, the same protective effect is exerted by a lower alkyl group, positioned ortho to the N-oxide (that is, when $R_8$ is lower alkyl, ortho to the N-oxide) when a lower alkoxy is, at the same time, positioned ortho to the carbonyl group on compound III starting material. In either of the above two instances, the lower alkoxy radical on compound III does not undergo conversion to a hydroxyl group.

A final compound II containing one or more hydroxyl substituents may be subjected to standard alkylation procedures in order to obtain the corresponding lower alkoxy substituents, if desired. Typically, such procedures involve the use of a dialkyl sulfate in the presence of base, such as sodium hydroxide; or the use of an alkyl iodide in the presence of a base, i.e., potassium carbonate. For methylation reactions, diazomethane may be used.

A final compound II containing one or more alkanoyl substituents may be obtained by subjecting the corresponding hydroxy substituted final compound to treatment with a lower alkanoic acid anhydride to convert hydroxyl substituents to lower alkanoyl substituents.

Compound III starting materials used in preparing the compounds of this invention are obtained as described in U.S. Pat. No. 611,282, filed Sept. 8, 1975. Thus, the compound III starting materials may be generally prepared by reacting a substituted benzoic acid ester with a substituted 2-picoline N-oxide in liquid ammonia in the presence of an alkali amide condensing agent. Typically, a sodium, potassium or lithium amide is used as the condensing agent. If one or more hydroxyl substituents are desired on the compound III, it is necessary to react a benzyloxy substituted benzoic acid with the 2-picoline N-oxide, using the same reaction conditions, and then subject the intermediate obtained to catalytic reduction (gaseous hydrogen and a palladium-on-carbon catalyst) to reduce the benzyloxy substituents present on the intermediate to the desired corresponding hydroxy groups.

Representative compound III starting materials which may be prepared by the above-described reactions include: 1-(3-chloro-4-hydroxyphenyl)-2-(2-pyridinyl)ethanone N-oxide, 1-(4-bromo-3,5-dihydroxyphenyl)-2-(2-pyridinyl)ethanone N-oxide, 1-(5-bromo-2-chlorophenyl)-2-(2-pyridinyl)ethanone N-oxide, 1-(3,5-diiodo-2-hydroxyphenyl)-2-(2-pyridinyl)ethanone N-oxide, 1-(5-bromo-2-chlorophenyl)-2-(6-methyl-2-pyridinyl)ethanone N-oxide, 1-(2,6-dimethoxyphenyl)-2-(2-pyridinyl)ethanone N-oxide, 1-(3-fluoro-4-methylphenyl)-2-(2-pyridinyl)ethanone N-oxide, 1-(3-hydroxy-4-methylphenyl)-2-(2-pyridinyl)ethanone N-oxide, 1-(3,4,5-triiodophenyl)-2-(2-pyridinyl)ethanone N-oxide, 1-(3-fluoro-4-methylphenyl)-2-(6-methyl-2-pyridinyl)ethanone N-oxide, and 1-(3-hydroxy-4-methylphenyl)-2-(6-methyl-2-pyridinyl)ethanone N-oxide.

Pharmaceutically acceptable, acid addition salts of the compounds of this invention are prepared according to conventional procedures by treating the free base form of the compounds of the invention in an alcoholic solution with the desired acid.

In the above formulas for the compounds of the invention, the R group definition may be more fully described as follows: the term "lower alkyl" is meant to include lower aliphatic hydrocarbons having from 1 to 7 carbon atoms, preferably 1 to 4 carbon atoms in the alkyl chain, such as methyl, ethyl, propyl, isopropyl, butyl, isobutyl and the like. This definition for lower alkyl also applies to the alkyl portions of the alkoxy, alkanoyl and alkanoic terms. The term "halogen" is meant to include bromine, chlorine, iodine and fluorine. The term "halide" is meant to include bromide, chloride and iodide.

The compounds of this invention having the formula I exhibit gastric anti-secretory activity when tested according to the procedures described by H. Shay et al., Gastroenterology, 5: 43 (1954). In this last-mentioned test, male Long Evans Hooded rats (150–200 gms.) are fasted for 24 hours prior to testing (water ad lib). Rats are randomly divided into groups of 5 rats each and housed individually. At the time of testing, each rat is lightly anesthetised with ether, its stomach exposed through a midline abdominal incision and the pylorus ligated with silk thread. The incision is sutured, closed and covered with Flexible Collodion, U.S.P. to prevent ingestion of blood. Test compound or vehicle control is administered (a) intraduodenally prior to closing the incision; (b) intraperitoneally immediately after ligation; or (c) orally as a one hour pretreatment. Four hours later, the rats are sacrificed by ether and their stomachs removed and opened.

Gastric contents are placed in centrifuge tubes and centrifuged to remove debree. The volume of gastric juice is measured (expressed in milliliters) and titratable acidity determined electrometrically to pH 7.4 (expressed as milliequivalents of acid per liter). Results are expressed as percent reduction of volume and/or titratable acidity from control group average. Reduced gastric acid secretion in experimental animals in the above-described test is considered to be representative of pharmacological utility in the treatment of hyperacidity in humans.

Thus, the compounds of the invention are active in the treatment of hyperactive conditions when administered to mammals at a dose level of from about 5 to about 20 mg/kg of body weight by the oral or parenteral route. This dosage may be varied depending on the severity of the condition, the age, weight, sex and class of mammal being treated, as well as the route of administration. For example, when 2-(2-hydroxy-5-methylphenyl)isoxazolo[2,3-a]pyridinium bromide (the compound of Example 4) is tested in the pylorus ligated rat in the above-described procedure, at a dose of about 20 mg/kg, intraperitoneally, a reduction of 66.3% in the volume of gastric acid and a reduction of 9.3% in the ion acid is obtained, compared to controls. Similarly, in this same test, 2-(2-methoxyphenyl)-7-methylisoxazolo[2,3-a]pyridinium bromide (the compound of Example 7) caused a reduction of 81.6% in the volume of gastric acid, compared to controls.

In addition to the pharmaceutical activity, the compounds of the invention are also useful as anti-inflammatory agents, as evidenced by results obtained in the carragennin-induced rat paw edema test. In this last-mentioned test, intact or adrenalectromized male albino rats (S-D derived) weighing 150–170 g. are arranged in groups of 10–15. The adrenalectromized rats, which are used one week after operation, are maintained with either 0.9% saline or hydrocortisone acetate (0.1 mg/animal). One hour after the administration of the test compounds (orally or parenterally), 0.05 ml of 1% carrageenin suspension is injected into the plantar area of the left hind paw. Three hours later, the difference between the left and right hind paws, which is measured by the displacement of mercury, is recorded. Results are expressed as percent change from the controls. This test is described in Arch. Internat. Pharmacodynam. Therap., 203: No. 1, 92–100, May 1973 by D. Pasquale, et al., and in the earlier work by Winter et al., Proc. Soc. Exp. Biol. N.Y., 111: 544, 1962.

Reduced inflammation in experimental animals in the above-described test is considered to be representative of pharmaceutical activity in the conditions where the soft tissues are inflamed, such as rheumatiod arthritis.

Thus, the compounds of the invention are active in the treatment of inflammatory conditions when administered to mammals at a dose level of from about 50 to about 100 mg/kg of body weight by the oral route. This dosage may be varied depending on the severity of the condition, the age, weight, sex and class of mammals being treated, as well as the route of administration. For example, when 2-(2-methoxyphenyl)-7-methylisoxazolo[2,3-a]pyridinium bromide (the compound of Example 7) is tested in the carrageenin-reduced rat paw edema test, at a dose of about 100 mg/kg, administered orally, a reduction of 40% in the amount of inflammation was obtained, compared to controls.

In use, the compound of the invention may be combined with pharmaceutically acceptable vehicles such as gum tragacanth in saline suspension to provide dosage forms for parenteral administration; or they may be combined with pharmaceutical diluents such as lactose, cornstarch, and the like and formulated into tablet or capsule dosage forms.

To further illustrate the practice of this invention, the following examples are included:

EXAMPLE 1

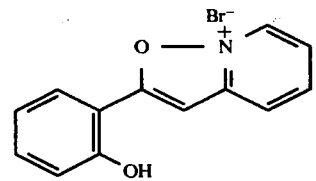

2-(2-Hydroxyphenyl)Isoxazolo[2,3-a]Pyridinium Bromide.

1-(2-Methoxyphenyl)-2-(2-pyridinyl)ethanone N-oxide (20.0 g) is refluxed under nitrogen for five hours in a mixture of 48% hydrobromic acid (250 ml) and glacial acetic acid (250 ml). The reaction mixture is cooled, and the solvents are removed under reduced pressure to give a solid product. Recrystallization from absolute ethanol gives pale yellow crystals (9.7 g, 40%), m.p. dec > 230° C.

Anal. Calcd. for $C_{13}H_{10}BrNO_2$: C, 53.45; H, 3.45; N, 4.80; Br, 27.35. Found: C, 53.38; H, 3.58; N, 4.66; Br, 27.33.

EXAMPLE 2

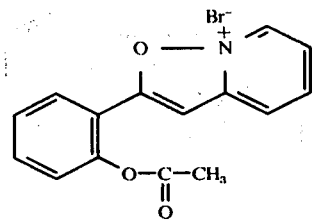

2-(2-Acetyloxyphenyl)Isoxazolo[2,3-a]Pyridinium Bromide.

2-(2-Hydroxyphenyl)isoxazolo[2,3-a]pyridinium bromide from Example 1 (5.0 g) is refluxed in acetic anhydride (40 ml) under nitrogen for 60–90 minutes. The solution is cooled, and the solvent is evaporated. The oily residue is diluted with ethyl acetate to crystallize the product. Recrystallization from isopropanol gives gray-white crystals (4.16 g, 73%), m.p. 198°–201° C.

Anal. Calcd. for $C_{15}H_{12}BrNO_3$: C, 53.91; H, 3.62; N, 4.19; Br⁻, 23.91. Found: C, 53.95; H, 3.81; N, 4.18; Br⁻, 23.83.

EXAMPLE 3

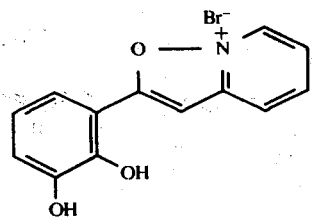

2-(2,3-Dihydroxyphenyl)Isoxazolo[2,3-a]Pyridinium Bromide.

Prepared by the procedure described in Example 1, using 1-(2,3-dimethoxyphenyl)-2-(2-pyridinyl)ethanone N-oxide. Recrystallization from absolute ethanol gives pale yellow crystals (13.5 g, 72%), m.p. dec > 222° C.

Anal. Calcd. for $C_{13}H_{10}BrNO_3$: C, 50.67; H, 3.27; N, 4.55; Br⁻, 25.93. Found: C, 50.50; H, 3.32; N, 4.40; Br⁻, 25.80.

EXAMPLE 4

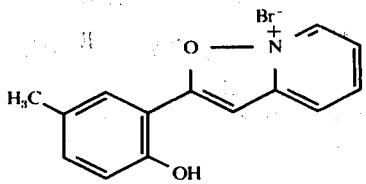

2-(2-Hydroxy-5-Methylphenyl)Isoxazolo[2,3-a]Pyridinium Bromide.

Prepared by the method described in Example 1, using 1-(2-methoxy-5-methylphenyl)-2-(2-pyridinyl)ethanone N-oxide. Recrystallization from absolute ethanol gives yellow crystals (22.65 g, 47.7%), m.p. dec > 220° C.

Anal. Calcd. for $C_{14}H_{12}BrNO_3$: C, 54.92; H, 3.95; Br, 26.10; N, 4.58. Found: C, 54.62; H, 4.05; Br, 25.94; N, 4.47.

EXAMPLE 5

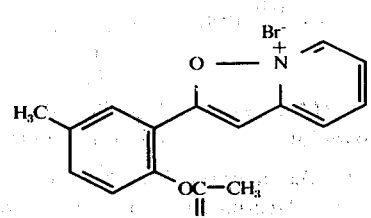

2-(2-Acetyloxy-5-Methylphenyl)Isoxazolo[2,3-a]Pyridinium Bromide.

Prepared by the method described in Example 2, from 2-(2-hydroxy-5-methylphenyl)isoxazolo[2,3-a]pyridinium bromide of Example 4. Crystallized on removal of solvents. Recrystallization from absolute ethanol gives white crystals (10.48 g, 76.5%), m.p. dec > 222° C.

Anal. Calcd. for $C_{16}H_{14}BrNO_3$: C, 55.19; H, 4.05; N, 4.02; Br⁻, 22.95. Found: C, 54.92; H, 4.09; N, 4.03; Br⁻, 22.96.

EXAMPLE 6

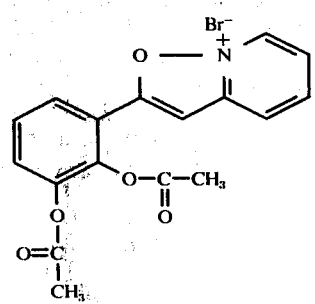

2-[2,3-Bis(Acetyloxy)Phenyl]Isoxazolo[2,3-a]Pyridinium Bromide.

Prepared by the method described in Example 2 using 2-(2,3-dihydroxyphenyl)isoxazolo[2,3-a]pyridinium bromide from Example 3 (6.5 g). Crystallized on removal of solvents. Recrystallization from absolute ethanol gives light beige crystals (6.75 g, 82%), m.p. 206–207° C.

Anal. Calcd. for $C_{17}H_{14}BrNO_5$: C, 52.06; H, 3.60; N, 3.57; Br⁻, 20.37. Found: C, 52.02; H, 3.86; N, 3.52; Br⁻, 20.33.

EXAMPLE 7

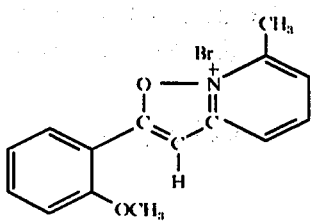

2-(Methoxyphenyl)-7-Methyl Isoxazolo[2,3-a]Pyridinium Bromide.

Prepared by the method described in Example 1 using crude 1-(2-methoxyphenyl)-2-(6-methyl-2-pyridinyl)ethanone N-oxide. Crystallized from absolute ethanol and recrystallization from same gives white crystals (1.69 g, 37.2%), m.p. dec > 220° C.

Anal. Calcd. for $C_{15}H_{14}BrNO_2$: C, 56.40; H, 4.38; N, 4.38; Br, 25.00. Found: C, 56.05; H, 4.42; N, 4.31; Br⁻, 25.08.

EXAMPLE 8

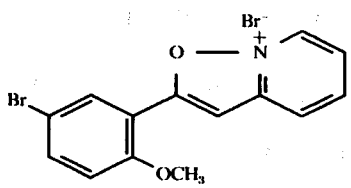

2-(2-Methoxy-5-Bromophenyl)Isoxazolo[2,3-a]Pyridinium Bromide.

Prepared by the method described in Example 1 using 1-(2-methoxy-5-bromophenyl)-2-(2-pyridinyl)ethanone N-oxide. Recrystallization from absolute ethanol gives pale yellow crystals (26.3 g, 76%), m.p. dec > 202° C.

Anal. Calcd. for $C_{14}H_{11}Br_2NO_2$: C, 43.56; H, 3.11; N, 3.63; Br, 41.51. Found: C, 42.29; H, 3.09; N, 3.58; Br, 40.57.

EXAMPLE 9

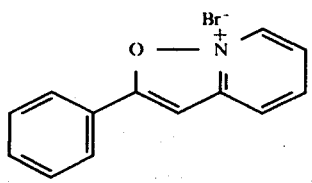

2-Phenylisoxazolo[2,3-a]Pyridinium Bromide.

Prepared by the procedure described in Example 1 using 1-phenyl-2-(2-pyridinyl)ethanone N-oxide. Recrystallization from absolute ethanol gives pale yellow crystals (2.32 g, 60%), m.p. 164°–165° C.

Anal. Calcd. for $C_{13}H_{10}BrNO$: C, 56.55; H, 3.65; N, 5.07; Br, 28.94. Found: C, 56.30; H, 3.95; N, 5.05; Br, 28.88.

EXAMPLE 10

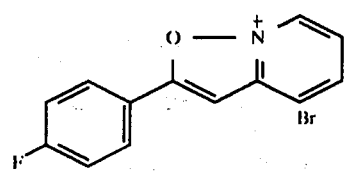

2-(4-Fluorophenyl)Isoxazolo[2,3-a]Pyridinium Bromide.

Prepared by the procedure described in Example 1 using 1-(4-fluorophenyl)-2-(2-pyridinyl)ethanone N-oxide. Recrystallization twice from isopropyl alcohol gives cream-colored crystals (10.6 g, 44%), m.p. 205°–207° C.

Anal. Calcd. for $C_{13}H_9BrFNO$: C, 53.09; H, 3.08; N, 4.76; F, 6.46; Br, 27.17. Found: C, 51.21; H, 3.23; N4.55; F, 6.52; Br (total), 26.77.

| Mass Spectrum | observed molecular ion | 295.9718 |
|---|---|---|
| | calculated for $C_{13}H_9Br^{81}FNO$ | 295.9851 |

EXAMPLE 11

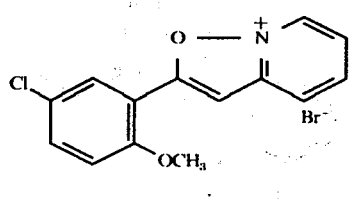

2-(5-Chloro-2-Methoxyphenyl)Isoxazolo[2,3-a]Pyridinium Bromide.

Prepared by the procedure described in Example 1 using 1-(5-chloro-2-methoxyphenyl)-2-(2-pyridinyl)ethanone N-oxide. Recrystallization from isopropyl alcohol gives off-white crystals (15.5 g, 45%), m.p. 208°–210° C.

Anal. Calcd. for $C_{14}H_{11}BrClNO_2$-: C, 49.37; H, 3.26; N, 4.11; Cl, 10.41; Br, 23.46. Found: C, 48.82; H, 3.22; N, 4.11; Cl, 10.33; Br, 23.23.

EXAMPLE 12

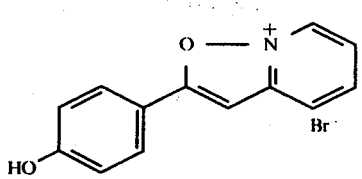

2-(4-Hydroxyphenyl)Isoxazolo[2,3-a]Pyridinium Bromide.

Prepared by the method described in Example 1 using 1-(4-methoxyphenyl)-2-(2-pyridinyl)ethanone N-oxide. Recrystallization twice from absolute ethanol gives yellow crystals (19.7 g, 58.6%), m.p. dec > 180° C.

Anal. Calcd. for $C_{13}H_{10}BrNO_2$: C, 53.45; H, 3.45; N, 4.80; Br, 27.35. Found: C, 53.25; H, 3.53; N, 4.71; Br, 27.09.

EXAMPLE 13

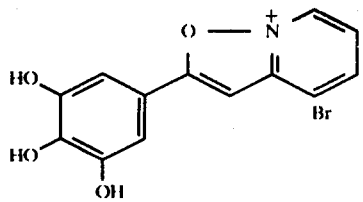

2-(3,4,5-Trihydroxyphenyl)Isoxazolo[2,3-a]Pyridinium Bromide.

Prepared by the method described in Example 1 using 1-(3,4,5-trimethoxyphenyl)-2-(2-pyridinyl)ethanone N-oxide. The solid product isolated is covered by a red-brown oil. This mixture is boiled in absolute ethanol and filtered. The pale yellow-brown crystals are washed with portions of absolute ethanol and then acetone, until the wash solvent is colorless, and sucked dry (8.0 g, 33.9%), m.p. dec > 210° C.

Anal. Calcd. for $C_{13}H_{10}BrNO_4$: C, 48.17; H, 3.11; N, 4.32; Br, 24.65. Found: C, 47.90; H, 3.18; N, 4.10; Br, 24.57.

EXAMPLE 14

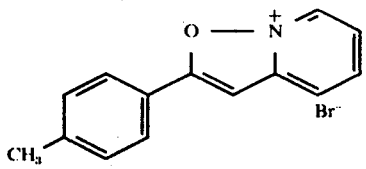

2-(4-Methylphenyl)Isoxazolo[2,3-a]Pyridinium Bromide.

Prepared by the procedure described in Example 1 using 1-(4-methylphenyl)-2-(2-pyridinyl)ethanone N-oxide. Recrystallization twice from absolute ethanol gives off-white crystals (1.75 g, 16.4%), m.p. 183°–186° C.

Anal. Calcd. for $C_{14}H_{12}BrNO$: C, 57.95; H, 4.17; N, 4.83; Br, 27.54. Found: C, 56.37; H, 4.33; N, 4.47; Br, 27.08.

| Mass Spectrum | observed molecular ion | 210.0910 |
|---|---|---|
| | calculated for $C_{14}H_{12}NO$ | 210.0919 |

We claim:

1. A process for preparing a compound having the formula II:

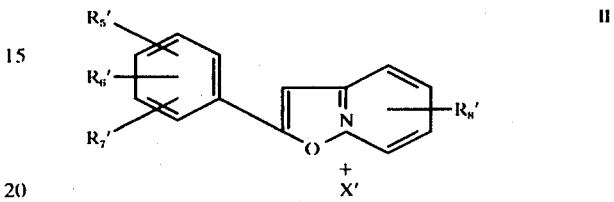

wherein $R_5'$, $R_6'$ and $R_7'$ are each hydrogen, halogen, hydroxy, lower alkyl, or lower alkoxy; $R_8'$ is hydrogen or lower alkyl and X' is a bromide, chloride or iodide salt, which comprises treating a compound of the formula III:

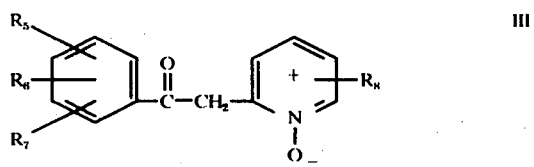

wherein $R_5$, $R_6$ and $R_7$ are each hydrogen, halogen, hydroxy, lower alkyl or lower alkoxy; and $R_8$ is hydrogen or lower alkyl with a hyrohalide acid and a lower alkanoic acid, compound II retaining said alkoxy groups only when compound III: (a) contains a halogen substituent on the phenyl para to alkoxy group or (b) said alkoxy group is ortho to the carbonyl and $R_8$ is lower alkyl ortho to the N-oxide.

2. A process according to claim 1 wherein, in an additional step, compound II is treated with a lower alkanoic acid anhydride to convert hydroxyl substituents to the corresponding lower alkanoyl substituents.

3. A process according to claim 1 wherein, in an additional step, compound II is alkylated to convert the hydroxyl substituents to the corresponding lower alkoxy substituents.

* * * * *

UNITED STATES PATENT OFFICE
CERTIFICATE OF CORRECTION

PATENT NO. : 4,018,781
DATED : APRIL 19, 1977
INVENTOR(S) : DAVID T. CONNOR, PATRICIA A. YOUNG, MAXIMILIAN VON STRANDTMANN

It is certified that error appears in the above-identified patent and that said Letters Patent are hereby corrected as shown below:

In Examples 7,10,12,13 and 14, "Br" in the structural formula should read ---$Br^-$---.

In Column 10, Claim 1, lines 12-22, that portion of the structural formula reading:

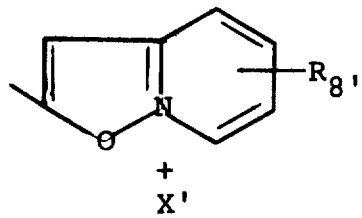

SHOULD READ

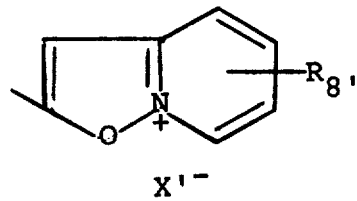

Signed and Sealed this

Twenty-ninth Day of November 1977

[SEAL]

Attest:

RUTH C. MASON
Attesting Officer

LUTRELLE F. PARKER
Acting Commissioner of Patents and Trademarks